Figure 1:
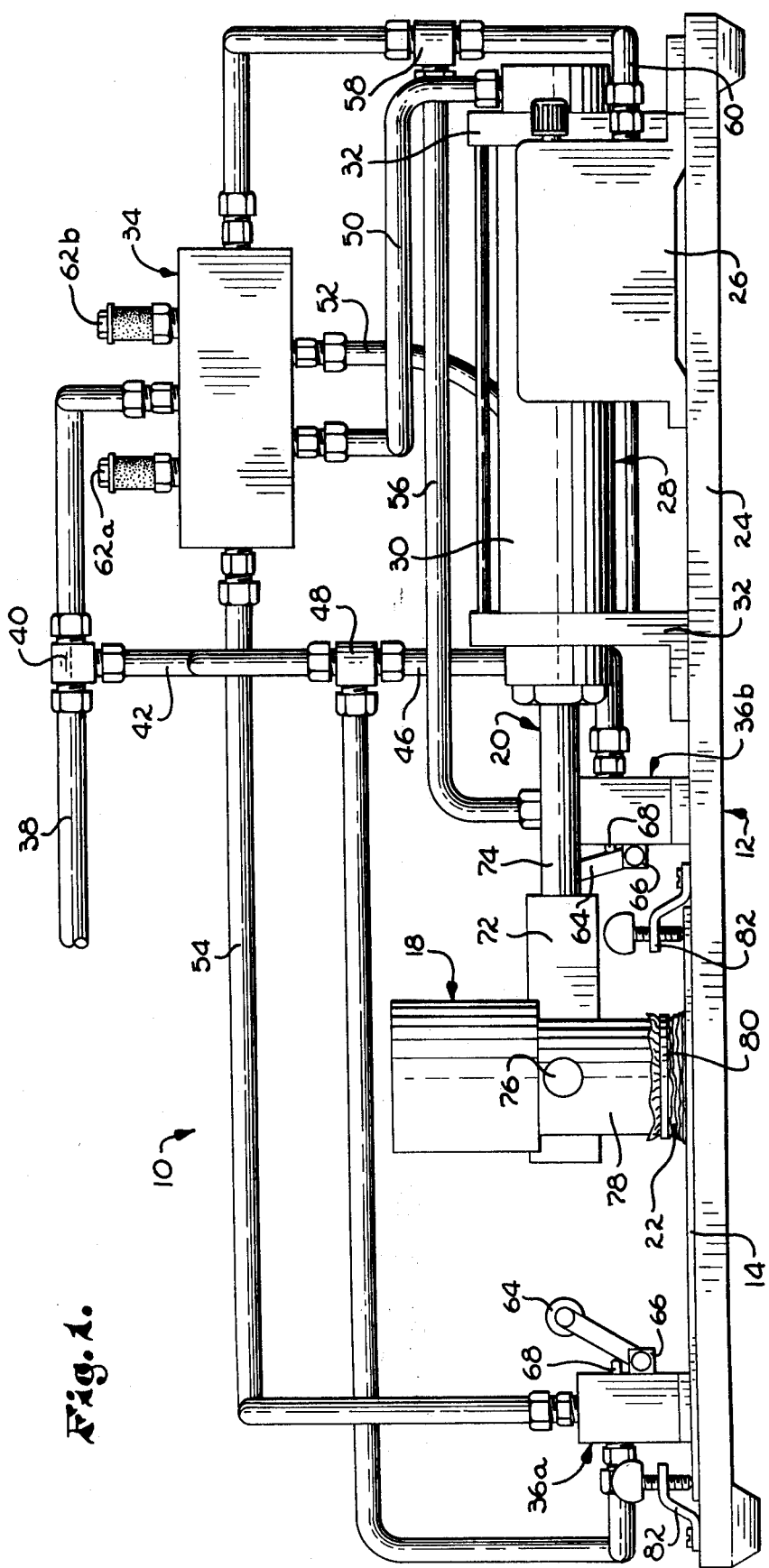

United States Patent [19]
Rooney et al.

[11] 3,974,678
[45] Aug. 17, 1976

[54] AUTOMATIC PAINT CURE TESTER

[75] Inventors: Robert L. Rooney, Ellicott; James W. Sautter, Pasadena, both of Md.

[73] Assignee: Conchemco, Incorporated, Lenexa, Kans.

[22] Filed: Mar. 5, 1975

[21] Appl. No.: 555,402

[52] U.S. Cl. .................................. 73/7; 73/150 R
[51] Int. Cl.² ...................................... G01N 3/56
[58] Field of Search ........................... 73/7, 150 R

[56] References Cited
UNITED STATES PATENTS

| | | | |
|---|---|---|---|
| 2,414,439 | 1/1947 | Brandon | 73/7 |
| 2,966,790 | 1/1961 | Walker | 73/7 |
| 3,040,559 | 6/1962 | Adams | 73/7 |
| 3,100,981 | 8/1963 | Engle et al. | 73/7 |
| 3,208,265 | 9/1965 | Rutledge | 73/7 |
| 3,293,912 | 12/1966 | Kochaney | 73/150 R |

OTHER PUBLICATIONS
*Washability Machine*, Henry A. Gardner Laboratory, Inc., Dec. 1941.

*Gardner Electrically Operated Straight-Line Washability Machine*, Henry A. Gardner Lab., Inc., May 1947.

*Primary Examiner*—Richard C. Queisser
*Assistant Examiner*—Joseph W. Roskos
*Attorney, Agent, or Firm*—Schmidt, Johnson, Hovey & Williams

[57] ABSTRACT

A testing device is capable of automatically performing a uniform and accurate test to determine the cure of a film of paint or the like on a test panel. The tester includes a powered rub weight wrapped, at its point of contact with the panel, with a solvent saturated material that rubs on the panel as the weight is caused to move back-and-forth along the painted surface. A drive mechanism shifts the rub weight, which is of a predetermined weight, at a constant length and speed of stroke and a counter records the number of strokes required for the solvent to penetrate the film.

4 Claims, 2 Drawing Figures

AUTOMATIC PAINT CURE TESTER

This invention relates to a testing device for obtaining an automatic, constant test for determining the cure of a film of paint or the like applied to a test panel. Heretofore the determination of whether or not a film of paint or the like was adequately cured was accomplished manually by the person conducting the test. The procedure would be to wrap a finger with cheesecloth and saturate the same with the proper solvent and then rub the painted surface of the panel. The degree to which the paint film had cured was determined by the resistance of the film to the solvent as measured by the amount of time that it took for the solvent to penetrate paint film to break the same down during rubbing. This manner of testing the paint cure was inaccurate in that each individual would use a different pressure and/or length of stroke and, consequently, the test result would vary from one individual tester to another because of the inconsistency of the tests.

It is, therefore, a very important object of our invention to provide an automatic paint cure tester to determine the cure of a film of paint or the like on a test panel in which the tester is capable of accurately performing the test in a consistent manner throughout the duration of the test.

A further object of our invention corresponding closely to that of the foregoing, is to provide a paint cure tester that is designed to eliminate human error in measuring the cure of a paint film.

Yet another object of the instant invention is to provide a paint cure tester in which the pressure of the rub weight on the panel and speed and length of stroke remains constant during the test.

Another object of the invention is to provide a paint cure tester capable of being set up to accurately duplicate a previous test while at the same time also having the capability of being set up to perform similar tests in which the rub weight pressure and length and speed of stroke may be selectively changed individually or in combination to suit the character of the paint film to be tested or the degree of cure desired.

A still further object of our invention is to provide a paint cure tester that can be conveniently located at the end of bake lines, coil coating lines, oven unloaders, etc. as well capable of being utilized in paint laboratories.

Figure 2:
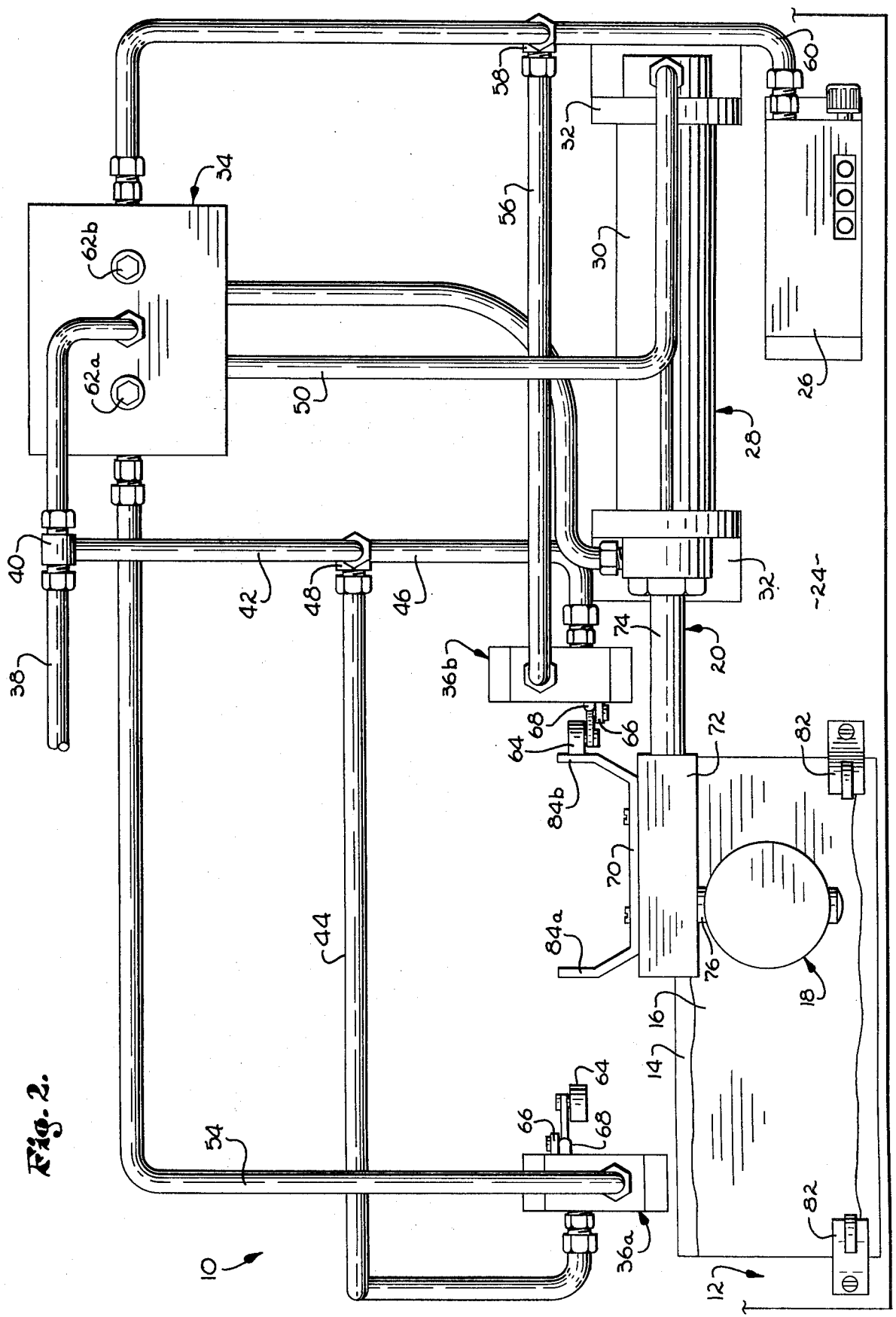

In the drawings:

FIG. 1 is a side elevational view of a paint cure tester made pursuant to the present invention; and FIG. 2 is a top plan view of the paint cure tester illustrating a test panel on which a film of paint or the like has been applied for testing the cure thereof.

A paint cure tester, generally designated by the numeral 10, is comprised of a fixture 12 adapted to receive and releasably hold a test panel 14 having a film of paint 16 or the like thereon to be tested; a weight 18 disposed to rest on the panel 14; a selectively actuatable drive mechanism broadly designated by the numeral 20 for reciprocating the weight 18 across the panel 14; and a solvent saturated material 22 carried by the weight 18 in a manner to be in contact with the film of paint 16. The fixture 12 includes a base 24 which serves as a support for the panel 14 and the drive mechanism 20, as well as a counter 26 coupled with the drive mechanism 20 for recording the number of cycles through which the latter is operated.

The drive mechanism 20 which, for the purpose of illustration is operated pneumatically includes, as its major components, a double-acting piston and cylinder assembly 28 having a cylinder 30 supported by a pair of mounting brackets 32 at either end thereof in a normally horizontal disposition relative to the base 24; a two-way air valve 34 suitably secured, such as on an upright back panel (not shown) on the fixture 12; a pair of three-way air valves 36a and 36b defining a pair of forward-reverse switches secured to the base 24; and a series of air conduits as will be hereinafter further identified, placing the components 28, 34 and 36a and 36b in communication with one another and an air supply source (not shown). It is to be understood that the piston and cylinder assembly 28, as well as the valves 34, 36a and 36b, along with the air counter 26 which is conveniently located on the base 24, are all of the kind readily available in the industry and well-known among those skilled in the art of pneumatic controls.

A supply of air for powering the drive mechanism 20 is provided via an air supply line 38 operably connected to a source of pressurized air, it being understood that the usual on-off switch, filter, regulator and lubricator (none of which are shown), are interposed between the line 38 and the air source. The air line 38 serves to place the valve 34 in communication with the air supply and includes a tee connection 40 from which a conduit 42 extends to place the valves 36a and 36b in uninterrupted communication with the air supply line 38 by way of conduits 44 and 46, respectively, and tee connection 48. Additionally, a conduit 50 places the valve 34 in communication with the piston and cylinder assembly 28 at the head end of the cylinder 30, while a conduit 52 interconnects the valve 34 with the assembly 28 at the piston rod end of the cylinder 30, thereby completing a two-way circuit between the piston and cylinder assembly 28 and the valve 34.

Communication between the valve 34 and the switching valves 36a and 36b is provided by conduits 54 and 56 respectively. A tee connection 58 is interposed in the conduit 56 in order that the air counter 26 might also be placed in communication with the conduit 56 by way of a line 60. A pair of mufflers or speed control silencers 62a and 62b are provided at the exhaust ports of the valve 34.

Each valve 36a and 36b is provided with a swingable cam follower head 64 and a corresponding mounting bracket 66 so located to depress an associated plunger 68 whenever the cam follower 64 is engaged by a generally U-shaped, laterally extending actuator 70 secured to a mounting block 72 defining the distal, free end of the piston rod 74 of the piston and cylinder assembly 28. A spindle 76 extends laterally from the block 72, opposite the actuator 70, on which the weight 18 is received and suitably secured thereon for disposition of its lower end 78 on the panel 14. Reference to FIG. 1 will show that the end 78 of the weight 18 is provided with multiple layers of absorbent material 22, such as cheesecloth, the material 22 being retained on the weight 18 by an elastic band 80 or the like.

In use, the panel 14, which may be made of metal, wood, plastic or similar material, is coated with a film of paint 16 or the like that is to be tested after a period of curing to determine whether or not the film has, in fact, been adequately cured. At the time of the test, the panel 14 is secured to the base 24 through the use of a pair of panel hold-down clamp assemblies 82 with the panel 14 presenting the paint film 16 in an upwardly facing direction. Once the panel 14 has been properly positioned, the rub weight 18 having the solvent saturated material 22 thereon is mounted on the spindle 76 such that the material 22 is between the weight 18 and the panel 14 in contact with the film 16 when the weight is resting on the panel. It is here to be noted that the type of solvent with which the material 22 is saturated will depend on the test to be conducted and the kind of film for which the cure is to be determined. The more frequently used solvents are methyl ethyl ketone, acetates, methyl isobutyl ketone, etc. and the size of the weight 18 is calculated to provide the amount of pressure needed to accomplish the particular test being run.

Once the panel 14 and rub weight 18 have been properly located, the drive mechanism 20 is actuated by introducing a supply of air into the supply line 38, at which time the entire system is energized with a supply of air being furnished to the valves 36a and 36b, as well as the valve 34. Presuming that each of the valves have their plungers disposed to locate the piston rod 74 in the disposition shown in FIG. 2, an arm 84b of the actuator 70 would have the plunger 68 of the valve 36b in a depressed condition, allowing a supply of air to proceed through the conduit 56 which would shift the plunger of the valve 34 to a disposition permitting air to flow from the latter into the head end of the cylinder 30 via the conduit 50. Introduction of air into the piston and cylinder assembly 28 in this manner would cause the piston rod 74 to move toward the left, viewing either of the Figures, causing the rub weight 18 with its material 22 to move across the paint film 16 on the panel 14. As the rod 74 is thus shifting, the air evacuating from the rod end of the cylinder 30 via the conduit 52, would be exhausting or venting through the speed control silencer 62b.

Full extension of the piston rod 74 causes an arm 84a of the actuator 70 to engage the cam follower 64 and thus depress the plunger 68 of the valve 36a. When this occurs, air is then permitted to flow through the conduit 54 to shift the plunger of the valve 34 in an opposite direction, causing the air supply to be cut off from the conduit 50 and directed through the conduit 52 to introduce air into the rod end of the cylinder 30 thus moving the piston rod 74 in an opposite direction or to the right when viewing the Figures. Accordingly, the air evacuates from the head end of the cylinder 30 via the conduit 50 and the speed control silencer 62a. Each time the valve 36b is actuated, the counter 26 is likewise actuated to record another cycle because of its being in communication with the conduit 56.

It is, of course, to be understood that not only is the amount of pressure placed on the panel 14 and therefore on the paint film 16, determined by the amount of weight used, but the speed at which the piston rod 74 reciprocates is determined by the setting of the adjustable silencers 62a and 62b, while the stroke length of the piston rod 74 may be predetermined and controlled by the spacing between the arms 84a and 84b on the actuator 70 so that a constant pressure, length and speed of the rubbing action of the material 22 on the film, is obtained. Thus, the saturated material 22 wets the panel 14 in a uniform manner as the weight 18 moves back-and-forth across the painted surface or film 16. The counter 26 records the number of strokes and when the paint film 16 is penetrated by the solvent the number of strokes are noted. If the number of strokes are equal to the predetermined amount of resistance needed for the particular paint film on the panel, the coating film is determined to be cured to the desired extent.

Therefore, there has been herein provided an automatic paint cure tested that has eliminated the human error inherent when such testing was accomplished by manually rubbing the painted panel with its resultant inconsistent pressures, speed and length of stroke. On the other hand, the instant invention has made it possible to provide an automatic and constant test in which the pressure, length and speed of each stroke can be predetermined and maintained to automatically accomplish the desired test. Furthermore, it will be recognized that the instant invention is readily adaptable to various coatings that may need to be tested by changing the weight to increase or decrease the pressure on the film as well as by selectively adjusting and/or changing the speed and length of stroke of the weight, depending on the particular requirements of the test. Also, the compactness of the tester makes it readily adaptable for use at the end of bake lines, coil coating lines, oven loaders, etc.

It is to be further understood that while the preferred form of the invention as herein disclosed utilizes a pneumatically powered drive mechanism, the spirit and intent of the invention might also be accomplished through other types of powered drive mechanisms.

Having thus described the invention, what is claimed as new and desired to be secured by Letters Patent is:

1. An automatic tester for performing consistently accurate and uniform tests to determine the cure of a film of paint or the like on a test panel, said tester comprising:
   a base provided with clamp means for releaseably receiving and holding said panel in a position to present said film of paint or the like in an upwardly facing direction;
   weight means of a selectively predetermined weight adapted to be placed on said panel;
   a quantity of absorbent material releaseably secured to said weight means in a disposition to be interposed between said weight means and said film when said weight means is placed on the panel;
   a selectively actuatable drive mechanism coupled with said weight means for repeatedly shifting the same across said panel along a predetermined path of travel with said material being in contact with the film,
   said drive mechanism including an elongate, reciprocably shiftable member having a distal end at which said weight means is attached,
   said material being saturated with a supply of solvent of a predetermined type corresponding to the test for which the cure of the film is to be determined; and
   control means located adjacent the panel at the opposite ends of said path of travel of said member and coupled with said drive mechanism for automatically reversing the direction of travel of said member when the latter engages said control means such that said solvent saturated material exerts a uniformly repetitious rubbing action on said film.

2. A tester as claimed in claim 1 wherein said member includes an actuator at said distal end engageable with said control means, said actuator being of a selectively predetermined configuration for determining the stroke length of said member in rubbing said material across the film.

3. A tester as claimed in claim 2 wherein said drive mechanism includes a selectively adjustable speed control means for determining the rate at which said material rubs the film.

4. A tester as claimed in claim 3 wherein there is included a counter operably coupled with said drive mechanism for recording the number of times said material is rubbed across the film.

* * * * *